United States Patent [19]

Bremer et al.

[11] 4,244,879

[45] Jan. 13, 1981

[54] PREPARATION OF MALEIC ANHYDRIDE

[75] Inventors: Noel J. Bremer, Kent; Dennis E. Dria, Spencer, both of Ohio

[73] Assignee: Standard Oil Company (Ohio), Cleveland, Ohio

[21] Appl. No.: 106,786

[22] Filed: Dec. 26, 1979

[51] Int. Cl.$^3$ ............................................. C07D 307/60
[52] U.S. Cl. ................................. 260/346.75; 252/437
[58] Field of Search ..................................... 260/346.75

[56] References Cited

U.S. PATENT DOCUMENTS

| | | | |
|---|---|---|---|
| 4,016,105 | 4/1977 | Kerr | 260/346.75 |
| 4,132,670 | 1/1979 | Katsumoto et al. | 252/437 |

FOREIGN PATENT DOCUMENTS 3431 8/1979 European Pat. Off. .

*Primary Examiner*—Henry R. Jiles
*Assistant Examiner*—Bernard Dentz
*Attorney, Agent, or Firm*—Joseph G. Curatolo; Herbert D. Knudsen; Larry W. Evans

[57] ABSTRACT

The present invention provides a method for the preparation of oxidation catalysts containing mixed oxides of vanadium and phosphorus, which catalysts are particularly effective in the oxidation of n-butane, n-butenes, 1,3-butadiene or a mixture thereof with molecular oxygen or an oxygen-containing gas in the vapor phase to produce improved yields of maleic anhydride with good selectivity. A vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound.

14 Claims, No Drawings

PREPARATION OF MALEIC ANHYDRIDE

BACKGROUND OF THE INVENTION

This invention relates to a method for preparing catalysts useful in the production of dicarboxylic acid anhydrides by the oxidation of hydrocarbons. More particularly it is directed to the preparation of catalysts suitable for producing maleic anhydride from 4-carbon atom hydrocarbons, such as n-butane, n-butenes, 1,3 butadiene or a mixture thereof.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. Conventional methods of preparing these catalysts involve combining a vanadium compound, a phosphorus compound, and if desired, promoter element compounds in a reducing medium under conditions which will provide vanadium in a valence state below +5 to form catalyst precursors capable of being converted to an oxide. The catalyst oxide precursor is then recovered and calcined to provide active catalytic material.

The use of gaseous HCl as a reducing agent for vanadium is disclosed in U.S. Pat. No. 4,002,650 where the vanadium and phosphorus components are present in an aqueous solution. The use of gaseous HCl as a reducing agent for vanadium is also described in U.S. Pat. No. 4,043,943 where the vanadium and phosphorus components are present in a liquid organic medium.

U.S. Pat. No. 4,016,105 describes the preparation vanadium and phosphorus oxide-containing catalysts, utilizing as reducing agents, organic acids or aldehydes, together with a co-reducing secondary alcohol. These reducing agents are added to an aqueous solution containing the vanadium and phosphorus components.

Similar preparational techniques are described in European Patent Appln. No. 3,431 in which the additional step of comminuting the vanadium-phosphorus precursor to a particle size of 500 to 700 microns (0.5 to 0.7 mm) is disclosed.

The use of such reducing agents as disclosed in the art, requires special precautions in the preparation of these catalysts because of the corrosive nature of the materials utilized.

A method for preparing catalysts containing vanadium and phosphorus oxides was described in U.S. Pat. No. 4,132,670 which required the maintenance of a solid phase and dispersion of the vanadium-containing feed compound. The method includes forming a vanadium-containing compound dispersion in an organic liquid medium such as alcohols, aldehydes, ketones, ethers or mixtures thereof, heating the dispersion to reduce the vanadium, and adding phosphoric acid in an organic solvent.

In the methods described above, separation of the catalyst precursor from the reaction solution has provided difficulties. Conventionally, the solution containing the precursor must be evaporated down, usually to a catalyst precursor-containing paste which must then be dried, broken up and ground. This provides difficulties for the commercial scale-up of the process, particularly where the catalyst precursor-containing solution includes flammable organic liquids. Where the solid phase dispersion has been maintained throughout the reduction of the vanadium and reaction with phosphoric acid, separation is more easily effected. In this instance, however, the catalyst obtained requires high operating temperatures when used to produce maleic anhydride, and produces modest yields of product.

SUMMARY OF THE INVENTION

It is therefore an object of the invention to provide a method of preparing vanadium and phosphorus-containing catalysts useful for the oxidation of 4-carbon atom hydrocarbons to produce maleic anhydride.

It is a further object of the invention to provide a method of preparing vanadium and phosphorus-containing catalysts useful for the oxidation of 4-carbon atom hydrocarbons to produce maleic anhydride, which catalysts exhibit improved yields and selectivity to maleic anhydride.

It is a further object of the invention to provide a method of preparing vanadium and phosphorus-containing catalysts useful for the oxidation of 4-carbon atom hydrocarbons to produce maleic anhydride which is simplified, economical and avoids the hazards of corrosion and/or flammability, and is capable of commercial scaleup.

It is a further object of the invention to provide a method of preparing vanadium and phosphorus-containing catalysts useful for the oxidation of 4-carbon atom hydrocarbons to produce maleic anhydride which includes improved recovery of catalyst precursors from the reaction medium.

These and other objects, together with the advantages thereof over known methods, which shall be apparent from the specification which follows, are accomplished by the invention as hereinafter described and claimed.

In general the process of the present invention comprises the steps of
(a) introducing a pentavalent vanadium-contain-compound into an organic liquid medium capable of at least partially solubilizing and reducing the vanadium to a valence state less than +5;
(b) effecting reduction of at least a portion of said vanadium to a valence state of +4;
(c) removing unsolubilized vanadium-containing compounds having a particle size greater than about 0.1 mm diameter;
(d) adding a phosphorus-containing compound to the reaction medium resulting from step (c) to form a catalyst precursor precipitate;
(e) recovering the catalyst precursor precipitate;
(f) drying the catalyst precursor precipitate;
(g) calcining the catalyst precursor precipitate to form the active oxidation catalyst.

The catalysts prepared by the above method are particularly effective in the oxidation of 4-carbon atom hydrocarbons such as n-butane, n-butenes, 1,3 butadiene or mixtures thereof with molecular oxygen or an oxygen-containing gas in the vapor phase to produce improved yields of maleic anhydride with improved selectivity. Essentially all the product produced in this oxidation process is maleic anhydride, with only minor amounts of lower acids being detected.

DETAILED DESCRIPTION OF THE INVENTION

In the method for the preparation of an oxidation catalyst containing the mixed oxides of vanadium and phosphorus, a vanadium compound, particularly a pentavalent vanadium compound, is at least partially solubilized in an organic liquid medium. Suitable vanadium compounds containing pentavalent vanadium include: vanadium pentoxide or vanadium salts, such as ammonium metavanadate and vanadium oxytrihalides. Vanadium pentoxide is preferred. To aid in solubilizing the vanadium, it is preferred that the vanadium-containing compound which is introduced into the liquid medium have a small particle size, and methods for further reducing particle size of the vanadium compound while in the liquid medium, such as by ball milling the initial suspension of vanadium in the liquid medium, may be employed.

The liquid medium employed must be capable of reducing at least a portion of the vanadium to a +4 valence state, either upon addition and solvation, or upon mixing and heating. In addition the liquid medium should be a solvent for phosphoric acid and be relatively unreactive towards phosphoric acid. The liquid medium must not, however, be a solvent for the mixed oxide of vanadium and phosphorus. Suitable liquid media for use in the invention are organic compounds such as alcohols, aldehydes, ketones, ethers and mixtures of the above. The organic liquid media used in the invention is preferably anhydrous. Preferred organic liquids suitable for use in this invention are alcohols, particularly isobutanol.

After the pentavalent vanadium compound is introduced into the liquid medium, reduction of the vanadium is effected, preferably by heating the resulting reaction medium, with stirring if desired. Preferred vanadium and phosphorus oxide catalysts for the oxidation of 4-carbon atom hydrocarbons to maleic anhydride contain vanadium in an average valence stage of about +3.9 to about +4.6. This average valence state is achieved when at least a portion of the pentavalent vanadium introduced into the reaction mixture is reduced to the +4 state, preferably about +4.1.

After partial reduction of the vanadium, unsolubilized vanadium-containing compounds should be removed from the reaction mixture. While the unsolubilized vanadium-containing compounds generally contain some portion of vanadium in a valence state less than +5, the greater portion of vanadium present remains in a +5 valence state. Although it is most preferred to remove all unsolubilized vanadium-containing compounds from the liquid medium after effecting reduction of the vanadium, removing all such unsolubilized vanadium-containing compounds having a particle size greater than about 0.1 mm diameter, results in the production of catalysts exhibiting excellent activity for the preparation of maleic anhydride, producing improved yields at high selectivity. In a preferred method of the invention, all unsolubilized vanadium-containing compounds having a particle size greater than about 0.04 to about 0.06 mm diameter are removed. Removal is achieved by conventional means, such as filtration, centrifugation, decantation and the like.

After removal of unsolubilized vanadium-containing compounds from the liquid reaction medium, a pentavalent phosphorus-containing compound is added to the reaction medium. Suitable phosphorus compounds containing pentavalent phosphorus include: phosphoric acid, phosphorus pentoxide, or phosphorus perhalide, such as phosphorus pentachloride. Phosphoric acid and phosphorus pentoxide are preferred. The pentavalent phosphorus-containing compound is preferably added to the reaction medium in the form of a solution of the phosphorus-containing compound in either a component of the liquid reaction medium, or in a liquid capable of yielding the phosphorus-containing compound to the liquid reaction medium. After addition of the phosphorus-containing compound to the liquid reaction medium, it is preferable to heat the liquid reaction medium with stirring, if necessary.

As stated above, the liquid medium employed should not be a solvent for the vanadium-phosphorus mixed oxide. Therefore, as the vanadium-phosphorus oxide catalyst precursor is formed, it precipitates out of the solution. The total $H_2O$ content of the medium, particularly at this point, should be below about 5%. The catalyst precursor precipitate is then recovered from the reaction medium by conventional methods including filtration, centrifugation and decantation.

The catalyst precursor precipitate is then dried and calcined at a temperature of 250° C. to 600° C. preferably in the presence of an oxygen-containing gas.

It is within the scope of this invention, to include promoter element-containing compounds in the reaction mixture at a suitable point in order that the catalyst precursor precipitate contain the promoter element.

Catalysts prepared by this method generally exhibit a phosphorus to vanadium ratio of about 1 to about 1.2:1. Preferred is a P/V ratio of about 1.1:1. The catalyst is activated by calcining it in air or an oxygen-containing gas at a temperature of 250° C. to 600° C. for a period of up to 5 hours or more. A preferred activation of the catalyst is accomplished by passing a mixture of steam and air or air alone over the catalyst at a temperature of about 300° C. to 500° C. for a period of about 1 to 5 hours.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 2 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of 350° C. to 500° C. being preferred.

The catalyst may be used alone or a support could be employed. Suitable supports include silica, alumina, Alundum, silicon carbide, titania, boron phosphate, zirconia, and the like. The catalysts may be used in a fixed-bed reactor using tablets, pellets or the like, or in a fluid-bed reactor using catalysts preferably having a particle size of less than about 300 microns. The contact time may be as low as a fraction of a second or as high as 50 seconds. The reaction may be conducted at atmospheric, superatmospheric or subatmospheric pressure.

EXAMPLES 1-4

80.0 grams $V_2O_5$ (99.5% powder) was introduced into 700 mm isobutanol (about 0.3% $H_2O$ content) with mechanical stirring and with reflux for about 16 hours.

The resulting slurry was olive green in color. This slurry was then filtered through a fritted filter funnel to yield a yellowish green solid ($V_2O_5$) and a dark amber filtrate. This filtration removed all unreacted $V_2O_5$ particles having a diameter greater then about 0.04 to about 0.06 mm, for a total of 50.1 grams $V_2O_5$ having been removed after drying. 37.38 grams of 100% orthophosphoric acid was dissolved in isobutanol and added to the filtrate. This mixture was refluxed for about 8 hours, and was then allowed to cool and stand. A bluish-green precipitate was then collected and dried for 2 hours at 150° C. The catalyst precursor was then tabletted with 1% graphite being added, in a Buehler press to 1⅛ inch (about 2.84 cm) diameter, requiring a pressure of about 4000 psig. The tablets were then calcined in air from 200° C. to 400° C. at a rate of 5° C. per minute, being held at 400° C. for 1 hour. The resulting catalyst had the formula $V_{1.0}P_{1.1}O_x$.

COMPARATIVE EXAMPLES 5-8

80.0 grams $V_2O_5$ (99.5% powder) was introduced into 700 ml isobutanol (about 0.3% $H_2O$ content) with mechanical stirring and was refluxed for about 16 hours. The resulting slurry was olive green and was not filtered. 100.0 grams of 100% orthophosphoric acid was dissolved in isobutanol and added to the slurry. The reaction mixture was refluxed for about 8 hours after which it was allowed to cool and stand. The suspension was then filtered to yield a greenish-blue solid which was dried, tabletted and calcined as in Examples 1-4. Tabletting in this instance, however, was more difficult and required a pressure of about 9000 psig. The resulting catalyst had the formula $V_{1.0}P_{1.1}O_x$.

The catalyst described in Examples 1-4 and Comparative Examples 5-8 were used to produce maleic anhydride from butane using a 20 cc fixed-bed reactor consisting of a length of stainless steel tubing having an outer diameter of about 1.3 cm and having a full length 0.31 cm axial thermowell. The reactor was heated with a split stainless steel block furnace. Flasks for receiving the product maleic anhydride were mounted in ice water, and tail gases were routed to a Carle Analytical Gas Chromatograph III for analysis. Reaction conditions and results of the tests run are described in Table I. The results are stated in terms as follows:

Single Pass Yield = Moles of Maleic Anhydride Formed/Moles of Butane Fed × 100

Total Conversion = Moles of Butane Reacted/Moles of Butane Fed × 100

Selectivity = (Single Pass Yield × 100)/Total Conversion

When the method of preparing catalysts containing mixed oxides of vanadium and phosphorus is employed according to the present invention, the hazards presented by using highly corrosive materials such as HCl gas are avoided. In addition, the vanadium and phosphorus-containing catalyst precursor can be separated from the reaction medium simply by filtration or similar methods, avoiding the hazards of evaporating off large quantities of flammable liquid. The liquid reaction medium produced by the method of the present invention, after the catalyst precursor has been removed, may easily be recycled for use in the reaction again.

As can be seen from the results listed in Table I, catalysts prepared according to the method of the invention effect yields and selectivities of 4-carbon atom hydrocarbons (such as butane) to maleic anhydride higher than the yields and selectivities effected by catalysts prepared by similar methods but without removal of unsolubilized vanadium-containing compounds before the addition of the phosphorus-containing compound to the reaction mixture. These higher yields are achieved at lower reaction temperatures, resulting in longer catalyst life and energy savings.

Additionally, post-preparation formation of the catalytic material into commercially usable forms is aided when the catalytic material utilized is prepared according to the method of the invention, as exhibited by the facilitated tabletting of the catalyst precursor material prepared by the method of the invention.

Thus it should be apparent to those skilled in the art that the subject invention accomplishes the objects set forth above. It is to be understood that the subject invention is not to be limited by the examples set forth herein. These have been provided merely to demonstrate operability, and the selection of vanadium and phosphorus-containing compounds, liquid media, promoter element-containing compounds if any, hydrocarbon feedstocks and reaction conditions can be determined from the total specification disclosure provided without departing from the spirit of the invention herein disclosed and described, the scope of the invention including modifications and variations that fall within the scope of the attached claims.

TABLE 1

Butane Feed Over $V_{1.0}P_{1.1}O_x$ Catalyst

| | Feed Ratio Air/HC | Contact Time (Sec.) | Temp. (°C.) Bath | Temp. (°C.) Exo. | Maleic Anhydride % Yield | Maleic Anhydride % Select. | Hrs. On Stream |
|---|---|---|---|---|---|---|---|
| Example No. | | | | | | | |
| 1 | 70/1 | 1 | 414 | 446 | 59.1 | 62.2 | 138.5 |
| 2 | 70/1 | 2 | 394 | 412 | 59.1 | 63.2 | 164.4 |
| 3 | 70/1 | 2 | 394 | 412 | 58.8 | 63.2 | 183.8 |
| 4 | 70/1 | 2 | 394 | 414 | 60.8 | 64.7 | 209.1 |
| Comparative Example No. | | | | | | | |
| 5 | 70/1 | 1 | 452 | 468 | 50.9 | 55.2 | 140.2 |
| 6 | 70/1 | 2 | 437 | 450 | 56.3 | 59.3 | 166.5 |
| 7 | 70/1 | 2 | 437 | 450 | 56.5 | 59.1 | 185.3 |
| 8 | 70/1 | 2 | 397 | 403 | 42.0 | 68.7 | 210.4 |

We claim:

1. A process for the production of maleic anhydride by the oxidation of n-butane, n-butene, 1,3 butadiene or a mixture thereof with molecular oxygen or oxygen-containing gas in the vapor phase at a reaction temperature of 250° C.–600° C. in the presence of a catalyst containing the mixed oxides of vanadium and phosphorus, wherein said catalyst is prepared by
(a) introducing a pentavalent vanadium-compound into an organic liquid capable of at least partially solubilizing and capable of reducing vanadium to a valence state less than +5 to form a reaction medium;
(b) effecting reduction of at least a portion of vanadium to a valence state of +4;
(c) removing unsolubilized vanadium-containing compounds having a particle size greater than about 0.1 mm diameter;
(d) adding a pentavalent phosphorus-containing compound to the reaction medium resulting from step (c) to form a catalyst precursor precipitate;
(e) recovering said catalyst precursor precipitate;
(f) drying said catalyst precursor precipitate;
(g) calcining said precipitate to form the active oxidation catalyst.

2. A process as recited in claim 1 wherein said organic liquid medium is essentially anhydrous.

3. A process as recited in claim 1 wherein reduction of said vanadium is effected by heating the vanadium-containing reaction medium of step (a).

4. A process as recited in claim 3 wherein reduction of said vanadium is effected by heating the vanadium-containing reaction medium of step (a) under reflux conditions.

5. The process as recited in claim 1 wherein said unsolubilized vanadium-containing compounds are removed by filtration.

6. A process as recited in claim 1 wherein said pentavalent phosphorus-containing compound is added to the reaction medium in the form of a solution of said pentavalent phosphorus-containing compound in said organic liquid.

7. A process as recited in claim 1 wherein said organic liquid is an alcohol.

8. A process as recited in claim 7 wherein said organic liquid is isobutanol.

9. A process as recited in claim 1 wherein said vanadium-containing compound is vanadium pentoxide.

10. A process as recited in claim 1 wherein said phosphorus-containing compound is orthophosphoric acid.

11. A process as recited in claim 1 wherein said oxidation catalyst is represented by the empirical formula:

$$V_1P_aO_x$$

wherein $a = 1.0$ to $1.2$ and x is the number of oxygens required to satisfy the valence requirements of the other elements.

12. A process as recited in claim 1 wherein said oxidation catalyst is represented by the empirical formula $V_1P_{1.1}O_x$.

13. A process as recited in claim 1 wherein unsolubilized vanadium-containing compounds having a particle size greater than about 0.06 mm diameter are removed.

14. A process as recited in claim 1 wherein unsolubilized vanadium-containing compounds having a particle size greater than about 0.04 mm diameter are removed.